United States Patent [19]

Lennox

[11] 4,338,488

[45] Jul. 6, 1982

[54] ELECTRONIC ARTIFICIAL LARYNX

[75] Inventor: Thomas M. Lennox, Mentor, Ohio

[73] Assignee: Luminaud Company, Mentor, Ohio

[21] Appl. No.: 70,851

[22] Filed: Aug. 29, 1979

[51] Int. Cl.$^3$ .............................................. A61F 1/20
[52] U.S. Cl. .................................... 179/1 AL; 3/1.3; 200/DIG. 2
[58] Field of Search ............ 179/1 AL, 121 C, 156 R, 179/156 A, 157; 3/1.3; 200/DIG. 2

[56] References Cited

U.S. PATENT DOCUMENTS

| | | | |
|---|---|---|---|
| 1,730,761 | 10/1929 | French | 179/121 C |
| 1,901,433 | 3/1933 | Burchett | 179/1 AL |
| 2,058,212 | 10/1936 | Burchett | 3/1.1 |
| 3,066,186 | 11/1962 | Trammell | 179/1 AL |
| 3,072,745 | 1/1963 | Barney | 179/1 AL |
| 3,084,221 | 4/1963 | Cooper et al. | 179/1 AL |
| 3,508,000 | 4/1970 | Snyder | 179/1 AL |

OTHER PUBLICATIONS

Edmund Lauder, Self-Help for the Laryngectomee, Chapter IV, "The Artificial Larynx," pp. 32–49, published 1971.
Aurex Corporation, "M-550 Intra-Oral Adapter With 'Neovox' M-520T Electro-Larynx".
D. H. Zwitman et al., "Experimental Modification of the Western Electric #5 Electrolarynx to a Mouth Type Instrument," Journal of Speech and Hearing Disorders-XL, 1, pp. 35–39.
A. W. Knox, "A Two-Way Conversion of the Western Electric Type 5 Artificial Larynx for Intra-Oral Usage," pp. 1–8.

Primary Examiner—Joseph A. Popek
Attorney, Agent, or Firm—Watts, Hoffmann, Fisher & Heinke Co.

[57] ABSTRACT

An electronic artificial larynx supported and operated without the use of an operator's hands. The electronic larynx includes a headband which fits securely around the operator's head. A switch is attached to the headband for opening and closing an electrical circuit that includes a signal generator and a tone generator. The switch has a displaceable actuator extending beyond the headband and adherable to the operator's forehead for movement with the forehead relative to the headband. A hollow, non-toxic plastic tube has one end rotatably connected to a stem of the tone generator and another end for placement in the operator's mouth. A linkage assembly connects the tone generator to the headband for permitting universal adjustment of positioning of the tube.

7 Claims, 8 Drawing Figures

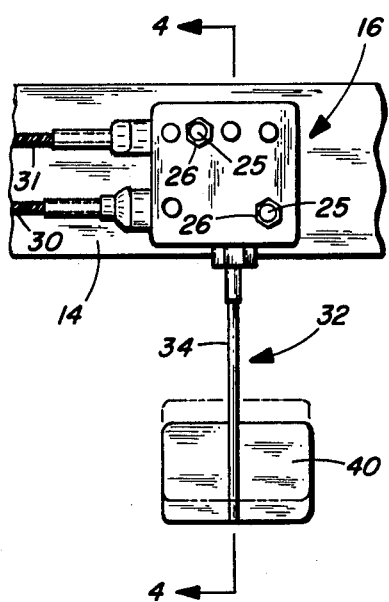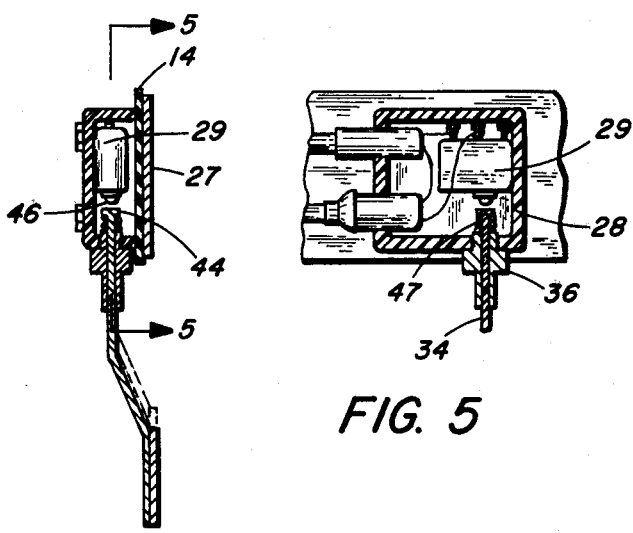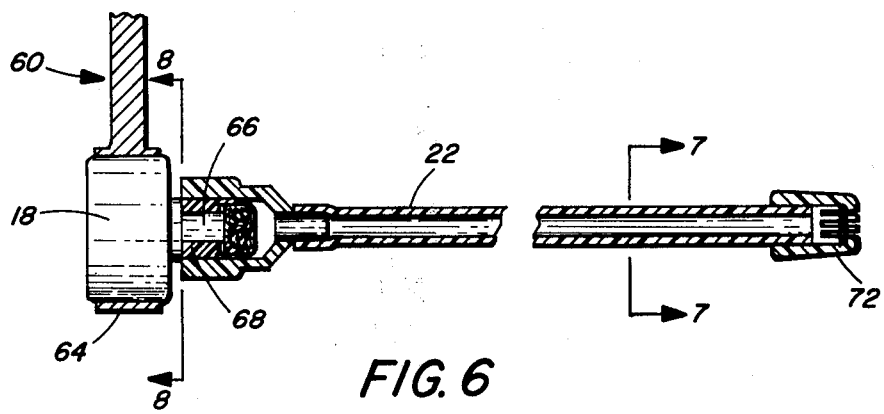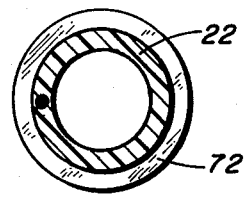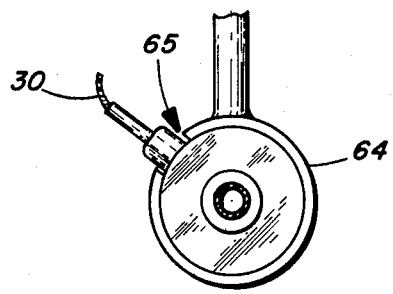

ELECTRONIC ARTIFICIAL LARYNX

BACKGROUND OF THE INVENTION

This invention relates to switches and support assemblies for electronic artificial larynxes.

Electronic artificial larynxes are used by persons who have had their diseased larynx or "voice box" removed. Invariably, the removal causes a person to lose the power of normal articulation of speech because the person can no longer produce a tone in the throat which can be modulated in the mouth into articulate speech. In those instances, electronic artificial larynxes are useful because they provide a tone substantially resembling the tone normally produced by the natural larynx.

Prior electronic artificial larynxes have been controlled by switches which shut off the electronic larynx to conserve a power source when the larynx is not in use. Often, the control switch was hand-operated and other parts of the electronic larynx were hand-held.

Problems arise with hand-operated or hand-supported electronic artificial larynxes when a would-be user is not able or does not desire to hold a component of the electronic larynx in his hand. This may occur when the user is physically unable to use his hands or when the would-be user desires to use his hands for other functions while he talks through the electronic larynx. Accordingly, a need exists for supports and switches for electronic artificial larynxes which enable the artificial larynx to be operated without use of the user's hands.

SUMMARY OF THE INVENTION

The present invention is an improved electronic artificial larynx that meets the above needs and others. The improved artificial larynx basically comprises a headband which fits securely around an operator's head, a switch attached to the headband for operating an electrical circuit that includes a pulse generator and a tone generator, a switch actuator extending beyond the headband operable to actuate the switch by movement of the operator's forehead relative to the headband, a hollow plastic tube having an end connected to the tone generator and an end for placement in the operator's mouth, and a linkage assembly connecting the tone generator and the tube to the headband for supporting the generator and tube adjacent the operator's mouth and for permitting universal adjustment of the tube.

By supporting the tone generator and its attached plastic tube by the headband, the tone generator and plastic tube can be supported without the use of the operator's hands. Further, by attaching the electronic switch to the headband for actuation in response to movement of the operator's forehead, the switch can be supported and operated hands-free.

An advantageous feature of the invention is the universal adjustability of the connection between the tone generator and the headband. This permits adaptation of the invention to accommodate the different shaped heads of possible users of the invention and also permits comfortable wearing by the users.

The above and other featues and advantages of this invention will become more apparent as the invention becomes better understood from the detailed description that follows, when considered in connection with the accompanying drawings.

BRIEF DESCRIPTION OF THE DRAWINGS

FIG. 3 is an enlarged fragmentary view of a headband and a switch assembly illustrated in FIG. 2;

FIG. 4 is a cross-sectional view taken along line 4—4 of FIG. 3;

FIG. 5 is a fragmentary view taken along line 5—5 of FIG. 4;

FIG. 6 is an enlarged fragmentary view of a tone generator and mouth tube illustrated in FIG. 2;

FIG. 7 is an enlarged view taken along line 7—7 of FIG. 6; and,

FIG. 8 is an enlarged view taken along line 8—8 of FIG. 6.

DETAILED DESCRIPTION OF THE PREFERRED EMBODIMENT

Figure 1:
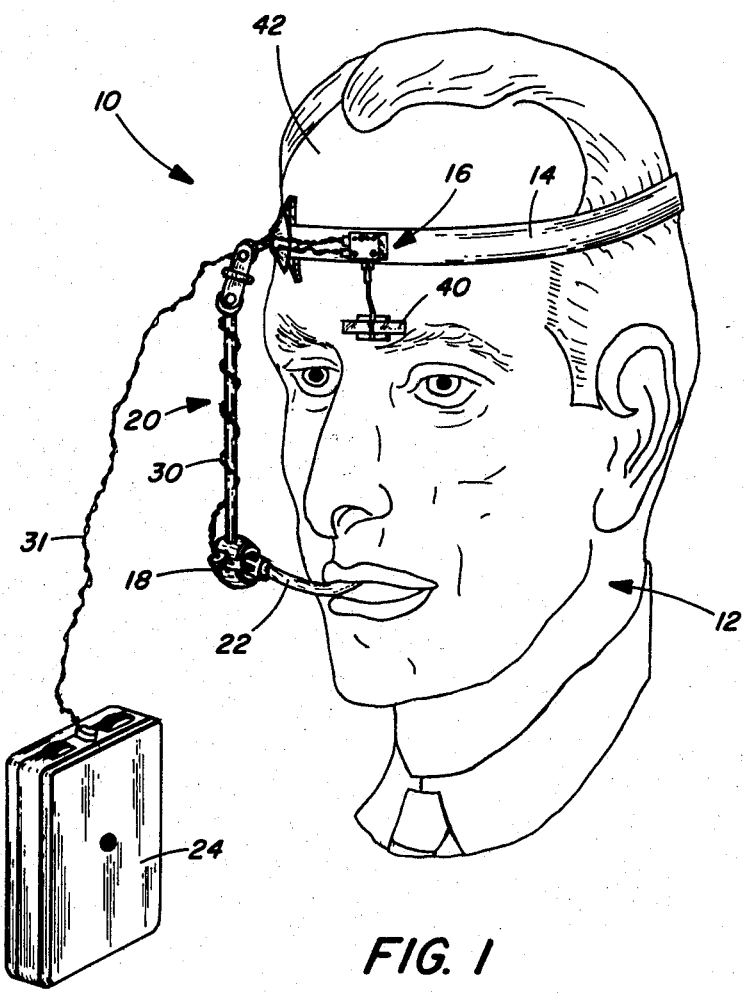
FIG. 1 is a perspective view of the present invention secured to a representative user of the invention.

Referring to the drawings, FIG. 1 illustrates an electronic artificial larynx generally designated by the reference numeral 10. The artificial larynx, secured to a representative operator or user 12, has a headband 14 that serves as a support, a switch assembly 16 supported by the headband for actuating the artificial larynx, a tone generator 18 supported by the headband, a linkage assembly 20 connecting the tone generator to the headband, a mouth tube 22 connected to the tone generator, and a signal generator 24 connected in electric circuit to the tone generator.

The headband 14 has an adjustable circumference size (the adjustability assembly not shown) and has a front portion adjacent the forehead of the user 12.

As best shown in FIGS. 3 and 4, the switch assembly 16 is attached to the front portion of the headband by two screws 25 and two nuts 26. The screws pass through a backing plate 27, the headband 14, and a switch housing 28. Backing plate 27 is of comparable size to the switch housing 28.

The switch assembly 16 includes a microswitch 29 attached in a series electrical circuit by a cable 30 to the tone generator 18 and by a cable 31 to the signal generator 24. The microswitch serves to open and close the electrical circuit of the invention to selectively operate the device.

A switch actuator 32 extends from the switch assembly beyond the headband 14. The actuator includes a vertically displaceable (i.e., reciprocable) stem 34 housed in a metal sleeve 36 threadedly attached to the switch housing 28. A paddle 40 is connected to one end of the stem 34 and (as best illustrated in FIG. 1) can be adhered by tape 40 or other suitable means, such as adhesive, to the user's forehead 42. When the user 12 desires to speak with the artificial larynx, the user moves the skin of his forehead in an upward direction, as by raising his eyebrows. Movement of the skin in this direction causes vertical movement of the secured paddle toward the headband 14 (represented by the phantom illustrations in FIGS. 3 and 4) and causes a head 44 of the stem to abut and depress an actuator button 46 of the microswitch 26, thus closing the electrical circuit of the tone and signal generators. When the artificial larynx is not in use (i.e., when the user 12 does not desire to speak the power source of signal generator 24 is shut-off and conserved by downward, vertical movement of the paddle in response to downward vertical movement of the skin of the forehead.

A compression spring 47, disposed between the stem head 44 and the sleeve 36, assures a close distance between the head and the microswitch 26 prior to adherance of the paddle 40 to the user's forehead. This assures that the user need only move the skin of his forehead a small distance to actuate the microswitch 26.

The signal generator 24 is adapted to generate electrical signals or pulses of energy representative of the plurality of frequencies contained within the complex acoustical wave of the audible tone normally developed by the natural larynx. The tone generator 18 is connected in electrical circuit to the signal generator by the cables 30, 31 and is responsive to signals from the generator 24 to transform the signals into an audible tone closely resembling the normally developed tone by the natural larynx. A signal generator and tone generator of this type is described in U.S. Pat. No. 3,066,186, the disclosure of which is incorporated herein by reference.

The signal generator 24 is sized to fit in a shirt pocket of the user 12 and has a clip (not shown) for securing the generator to the pocket.

Figure 2:
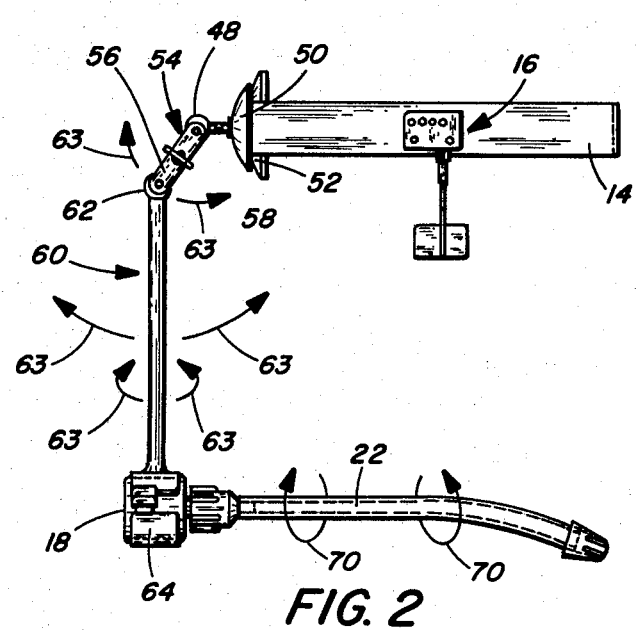
FIG. 2 is a fragmentary plan view of the invention illustrated in FIG. 1.

As best illustrated in FIGS. 1 and 2, the headband 14 supports the mouth tube 22 and the tone generator 18 by the linkage assembly 20. The linkage assembly includes a stationary ball 48 connected to a cupped metal base 50 attached to the outer surface of the headband. A cupped elastomeric pad 52 is attached to the inner surface of the headband and avoids possible discomfort of the base to the user 12.

A rotatable socket assembly 54 has two spaced parallel arms 56 (only one arm being shown due to the direction of viewing in the drawings), with an adjusting screw 58 passing through a bore in each arm to control the distance between the spaced arms. The bore in the unshown arm is threaded and the bore in the shown arm 56 is unthreaded to permit movement of the arms toward or away from one another in response to rotation of the adjusting screw 58. The arms define a socket at each of the two ends of the socket assembly 54. One of the two end sockets surrounds a portion of the stationary ball 48 to form a ball joint that permits rotation of the socket assembly 54 about the ball 48.

A boom 60 is attached to the other end socket of the socket assembly 54 by a ball 62 integral with one end of the boom. The ball 62 and the associated end socket form a ball joint that permits rotation of the boom relative to the socket assembly 54. Rotation of the socket assembly 54 about the balls 48, 62 (exemplified by the arrows 63 in FIG. 2) permits universal adjustment of the positioning of the boom 60 relative to the headband 14.

The other end of the boom 60 has a hollow cylindrical housing 64 (FIGS. 6 and 8). As best shown in FIG. 8, the housing 64 supports and substantially surrounds the tone generator 18. The housing has a gap 65 to permit connection of the cable 30 to the tone generator. Since the positioning of the boom is universally adjustable relative to the headband, so is the tone generator.

The mouth tube 22 is hollow, plastic, and non-toxic. As best shown in FIG. 6, one end of the tube is connected to a stationary stem 66 of the tone generator 18. A plastic sleeve 68 is fixedly secured inside one end of the tube 22 and surrounds the stem 66 to permit rotation of the mouth tube about the stem (exemplified by arrows 70 in FIG. 2). The other end of the mouth tube is for placement in the user's mouth (as shown in FIG. 1) and has a filter 72 for inhibiting entry of moisture from the mouth.

While a preferred embodiment of the invention has been disclosed in detail, various modifications or alterations may be made therein without departing from the spirit and scope of the invention set forth in the appended claims.

What is claimed is:

1. In an electronic artificial larynx having a tone generator and a signal generator, the improvement comprising:
   (a) a headband for secure fitting around a human head adjacent the forehead;
   (b) a switch attached to the headband for opening and closing an electrical circuit that includes the signal generator and tone generator;
   (c) a switch actuator extending beyond the headband and movable transversely of the headband to actuate the switch, means forming a part of the actuator extending from the headband adherable to the forehead for movement therewith relative to the headband;
   (d) a hollow, non-toxic plastic tube having an end rotatably connected to a stem of the tone generator and an end for placement in the mouth of the head;
   (e) linkage means carrying the tone generator and the tube for permitting universal adjustment for positioning of the tube, the linkage means including:
      (i) a ball connected in stationary relationship to the headband;
      (ii) a rotatable socket assembly having an arm with two sockets, one at each end of the arm;
      (iii) one of the sockets surrounding a portion of the ball that is connected to the headband;
      (iv) a boom having two ends;
      (v) a ball connected in stationary relationship to one end of the boom;
      (vi) the other socket surrounding a portion of the ball that is connected to the boom; and,
      (vii) the other end of the boom adapted to support the tone generator.

2. In an electronic artificial larynx having a tone generator and a signal generator, the improvement comprising:
   (a) a headband for secure fitting around a human head adjacent the forehead;
   (b) a switch attached to the headband for opening and closing an electrical circuit that includes the signal generator and tone generator;
   (c) a switch actuator extending beyond the headband and movable transversely of the headband to actuate the switch, the actuator including paddle means attachable to the forehead and being operable by movement of the forehead relative to the headband;
   (d) a hollow, non-toxic plastic tube having an end connected to the tone generator and an end for placement in the mouth of the head;
   (e) linkage means carrying the tone generator and the tube for permitting universal adjustment for positioning of the tube, the linkage means including:
      (i) a ball connected in stationary relationship to the headband;
      (ii) a rotatable socket assembly having an arm with two sockets, one at each end of the arm;
      (iii) one of the sockets surrounding a portion of the ball that is connected to the headband;
      (iv) a boom having two ends;

(v) a ball connected in stationary relationship to one end of the boom;

(vi) the other socket surrounding a portion of the ball that is connected to the boom; and, (vii) the other end of the boom adapted to support the tone generator.

3. In an electronic artificial larynx having a tone generator and a signal generator, the improvement comprising:

(a) a headband for secure fitting around a human head adjacent the forehead;

(b) a switch attached to the headband for opening and closing an electrical circuit that includes the signal generator and tone generator;

(c) a switch actuator extending beyond the headband and movable transversely of the headband to actuate the switch, means forming a part of the actuator extending from the headband adherable to the forehead for movement therewith relative to the headband;

(d) a hollow, non-toxic plastic tube having an end connected to the tone generator and an end for placement in the mouth of the head; and, (e) linkage means connecting the tone generator and the tube to the headband for permitting universal adjustment of positioning of the tube.

4. The artificial larynx of claim 3 wherein the tube end connected to the tone generator is rotatably connected to a stem of the tone generator.

5. An apparatus for supporting a tone generator of an electronic artificial larynx, comprising:

(a) said tone generator;

(b) a hollow, non-toxic plastic tube having an end connected to the tone generator and an end for placement in the mouth of a user's head;

(c) a headband for secure fitting around said user's head;

(d) linkage means carrying the tone generator and the tube for permitting universal adjustment for positioning of the tube, the linkage means including:

(i) a ball connected in stationary relationship to the headband;

(ii) a rotatable socket assembly having an arm with two sockets, one at each end of the arm;

(iii) one of the sockets surrounding a portion of the ball that is connected to the headband;

(iv) a boom having two ends;

(v) a ball connected in stationary relationship to one end of the boom;

(vi) the other socket surrounding a portion of the ball that is connected to the boom; and, (vii) the other end of the boom adapted to support the tone generator.

6. The apparatus of claim 5 wherein the tube end connected to the tone generator is rotatably connected to a stem of the tone generator.

7. An apparatus for operating a tone generator of an electronic artificial larynx, comprising:

(a) a headband for secure fitting around a human head adjacent the forehead;

(b) a switch attached to the headband for operating the tone generator; and, (c) a switch actuator extending beyond the headband, movable relative to the headband to actuate the switch, and including paddle means adherable to the forehead for movement therewith relative to the headband for actuating said switch and said tone generator.

* * * * *